(12) United States Patent
Signorino et al.

(10) Patent No.: US 7,858,129 B2
(45) Date of Patent: Dec. 28, 2010

(54) HIGH GLOSS FILM COATING AND STABLE SOLUTION THEREFOR

(75) Inventors: Charles Signorino, Norristown, PA (US); Terry L. Smith, Pottstown, PA (US)

(73) Assignee: Emerson Resources, Inc., Norristown, PA (US)

( * ) Notice: Subject to any disclaimer, the term of this patent is extended or adjusted under 35 U.S.C. 154(b) by 0 days.

(21) Appl. No.: 11/163,734

(22) Filed: Oct. 28, 2005

(65) Prior Publication Data

US 2006/0040042 A1 Feb. 23, 2006

Related U.S. Application Data

(63) Continuation of application No. 10/636,156, filed on Aug. 7, 2003, now abandoned.

(51) Int. Cl.
*A23L 1/00* (2006.01)

(52) U.S. Cl. .......................... 426/89; 426/302; 426/661

(58) Field of Classification Search ................. 426/661, 426/302, 89, 658
See application file for complete search history.

(56) References Cited

U.S. PATENT DOCUMENTS

| 3,390,049 | A | * | 6/1968 | Reduick et al. | 424/481 |
| 4,725,441 | A | * | 2/1988 | Porter et al. | 424/479 |
| 4,828,841 | A | | 5/1989 | Porter et al. | 424/479 |
| 5,059,248 | A | * | 10/1991 | Signorino et al. | 106/402 |
| 5,480,479 | A | | 1/1996 | Signorino | 106/162 |
| 6,395,298 | B1 | | 5/2002 | Flanagan et al. | 424/479 |
| 6,620,431 | B1 | * | 9/2003 | Signorino | 424/451 |

* cited by examiner

*Primary Examiner*—Leslie Wong
(74) *Attorney, Agent, or Firm*—William D. Hare; McNeely, Hare & War, LLP

(57) ABSTRACT

A coating composition for use in coating foods, confections, nutraceuticals and pharmaceuticals is comprised of shellac in aqueous solution, a hydrolyzed starch product having a dextrose equivalent of 10 or greater and an effective amount of a plasticizer. The coating composition provides a surprisingly high gloss coating. The edible film coating composition solution may be stabilized by adding an effective amount of ethylene diamine tetraacetic acid salt wherein the solution may remain stable for at least three months. The ethylene diamine tetraacetic acid salt may include disodium, trisodium and tetrasodium salts of ethylene diamine tetraacetic acid. Preferably, the concentration of ethylene diamine tetraacetic acid is about 0.5% to 2% of the solution.

33 Claims, No Drawings

HIGH GLOSS FILM COATING AND STABLE SOLUTION THEREFOR

REFERENCE TO RELATED APPLICATIONS

This application is a continuation of U.S. patent application Ser. No. 10/636,156, filed Aug. 7, 2003 now abandoned, and is hereby incorporated by reference.

BACKGROUND OF THE INVENTION

There is a need to film coat tablets in the pharmaceutical and the nutraceutical industries. However, the coating of tablets to date has usually provided a low gloss and a disagreeable slimy mouth feel. Even clear unpigmented films do not present a high gloss finish.

One attempt at coating in the past was to use hydroxypropyl methyl cellulose (HPMC) as described in my previous patent, U.S. Pat. No. 5,480,479. Other efforts have been made by others in attempts to improve the appearance and organoleptic properties of coated tablets. For example, see U.S. Pat. No. 4,828,841—Porter et al. which uses alginates to attempt to improve gloss. Also, attention is directed to U.S. Pat. No. 6,395,298—Flanagan which uses the gum gellan to attempt to produce gloss. Both of these efforts have not been satisfactory. The coating method disclosed by Porter et al. produces a finish which is hazy after a build up of material. Flanagan is very hard to prepare and apply and cannot be used at concentrations above 2% gum solids in the coating suspension.

SUMMARY OF THE INVENTION

The present invention provides an edible film coating composition for use in coating foods, confections, nutraceuticals and pharmaceuticals which produces a surprisingly high gloss.

Another advantage of the present invention is that it may be used to produce a clear coating system which adds gloss to previously color coated tablets or uncoated tablets.

Another advantage of the present invention is to provide a coating composition which may contain plasticizers and colorants to film coat foods, confections, nutraceuticals and pharmaceuticals with a high gloss.

Another advantage of the present invention is to provide a coating composition that is easily prepared and applied to foods, confections, nutraceuticals and pharmaceuticals using standard equipment and procedures.

In accordance with one aspect of the present invention, an edible film coating composition for use in coating foods, confections, nutraceuticals and pharmaceuticals comprises shellac in an aqueous solution, a hydrolyzed starch product having a dextrose equivalent of 10 or greater and an effective amount of a plasticizer for making the coating composition non-sticky when applied as a coating wherein a surprisingly high gloss finish coating is achieved.

Another aspect of the present invention is to provide the aforesaid edible film coating composition which produces a surprisingly high gloss coating composition solution which has a shelf life of three or more months.

An advantage of this aspect of the present invention is that the coating composition may be prepared by a coating manufacturer and shipped to a facility that performs the coating operation.

In accordance with this aspect of the present invention, a stable coating solution for use in forming an edible film coating comprises shellac in aqueous solution, a hydrolyzed starch product having a dextrose equivalent of 10 or greater, an effective amount of a plasticizer for making the coating composition non-sticky when applied as a coating and an effective amount of ethylene diamine tetraacetic acid salt (EDTA salt) wherein the solution remains stable for at least three months.

In accordance with the present invention, the solution may be maintained stable with up to 40% solids. In a presently preferred embodiment, an effective amount of ethylene diamine tetraacetic acid salt may be in the neighborhood of 0.5% to 2% of the solution, although it is understood that it may be less or more.

In accordance with the present invention the preferred salts of ethylene diamine tetraacetic acid include disodium, trisodium and tetrasodium salts.

DETAILED DESCRIPTION OF THE INVENTION

Surprisingly, in accordance with the present invention, shellac deposited out of water may be used as a component of a film forming system to produce a high gloss coating composition. Aqueous based shellac is utilized in the present invention. Aqueous based shellac would be ammoniated shellac to make the shellac soluble in water.

In accordance with the present invention, an aqueous shellac or ammoniated shellac in water may be utilized with a hydrolyzed starch product such as a maltodextrin with a dextrose equivalent (DE) greater than 10 or a dry glucose syrup with a DE above 20 and an effective amount of a plasticizer.

The aqueous shellac may be any suitable ammoniated shellac dissolved in water, but such shellacs are commercially available under the trademarks MARCOAT™ 125 and EMCOAT™ 120 available from Emerson Resources, Inc., 600 Markley Street, Norristown, Pa. 19401. MARCOAT™ 125 is an aqueous shellac glaze having 25% shellac in water, EMCOAT™ 120 is an aqueous shellac glaze having 20% shellac in water. All percentages herein, unless otherwise indicated, are expressed as percentages by weight.

Various hydrolyzed starch products may be utilized including maltrodextrins with a DE greater than 10 and dried glucose syrups which have a DE above 20. Suitable hydrolyzed starch products are commercially available from Grain Processing Corporation of Muscatine, Iowa under trademarks such as MALTRIN M200, MALTRIN 180 and MALTRIN 250. MALTRIN M200 is a hydrolyzed starch product having a DE of 20 and MALTRIN 180 is a hydrolyzed starch product having a DE of 18, etc. It is presently preferred to use a hydrolyzed starch product having a DE of 18 in the coating composition of the present invention.

Compositions of the shellac and hydrolyzed starch products such as MALTRIN M200 may be blended at a ratio of 1:1 and as high as 1:5. Ratios having one part shellac to two or three parts of hydrolyzed starch product give a good gloss and balance shellac's sealing and taste masking with the hydrolyzed starch's solubility and good mouth feel.

This composition of the film formers of shellac and hydrolyzed starch product may be modified with a suitable plasticizer in an effective amount to create evenness of the coating and reduce stickiness. Plasticizers may be used in the composition at 1 to 25% of the combined weight of the shellac and hydrolyzed starch product (film formers) of the composition. The plasticizer level is determined by the type of plasticizer used, the ratio of shellac to hydrolyzed starch product, and the level to which the composition may be pigmented. Plasticizers may be selected from the group including triacetin (TA), triethylcitrate (TEC), polyethylene glycol (PEG) (molecular weight (MW) 200-8000), propylene glycol (PG), glycerine, glycerol monostearate (GMS), diacetylated monoglyceride (DAM) and polysorbate 80 (PS80) (and other molecular weights of polysorbate). As may be seen from the examples hereinafter provided, typical amounts of plasticizer range in the neighborhood of 1% to 2% of the solution, although the level may be lower or higher.

This unique and surprising film coating composition may be further modified with colorants to produce various colors. Further, the unique system of this film coating composition may be modified with flavors, sweeteners and other organoleptic enhancers without causing adverse effects on the gloss of the coating.

Various colorants may be utilized in the high gloss composition of the present invention including FD&C lakes and dyes, D&C lakes and dyes, titanium dioxide, iron oxides, pigments deposited on mica powder (micanized pigments) and other natural colorants. Colorants may be added to the system at up to 20% to 40% of the combined weight of the shellac and hydrolyzed starch product.

The edible film coating composition of the present invention provides surprisingly high gloss. Using the TRICOR Surface Analysis System, Model 805A, to measure surface gloss, typical finishes on film coated products give readings up to 150. With the standard clear coat of resins currently used, the gloss values may be raised to approach 200. With the aqueous based shellac/hydrolyzed starch product composition of the present invention, gloss values above 250 may be readily achieved. Further, in accordance with the present invention, film coating compositions formulated with aqueous shellac and various hydrolyzed starch products at several different ratios, with selected plasticizers, give this very surprising result.

The following are some examples to illustrate the present invention and are given by way of illustration and not by way of limitation. In each of the examples illustrated below, the aqueous shellac was obtained from MARCOAT™ 125 which is a 25% solids solution, that is, it contains 25% shellac. In each of the following example formulations, they are based on a total of 100 parts by weight. In each example where the quantity of MARCOAT™ 125 is indicated, the shellac is 25% of the quantity indicated, since MARCOAT™ 125 is a 25% shellac solution. For example, in Example 1, 12 parts of MARCOAT™ 125 are indicated, which would result in 3 grams of shellac solids if 12 grams of MARCOAT™ 125 were used.

In Example 1 indicated below, a typical clear coating solution was prepared by dissolving the hydrolyzed starch product and the polyethylene glycol in water and then adding the MARCOAT™ 125 which is a 25% solution of shellac in water. In all examples, illustrated herein, it is preferred to use deionized water.

Example 1

| Material | Quantity |
| --- | --- |
| MARCOAT ™ 125 | 12 |
| Hydrolyzed Starch Product (DE 20) | 6 |
| Polyethylene Glycol (MW 8000) | 1 |
| Water | 81 |

Example 1 produces 10% solids, namely 3 grams of shellac, 6 grams of maltodextrin (from Maltrin M200) and 1 gram of polyethylene glycol, assuming the measurements are in gram.

The coating composition of Example 1 or the other coating composition examples to be described herein may be applied to tablets which have been coated or tablets which are uncoated. The application may be made in a fluid bed coater or a standard side vented pan. Using standard spray guns and coating parameters, a glossy film may be easily applied. As little as 0.25% weight gain may supply the gloss desired on coated tablets. More coating may be applied, especially if a seal on an uncoated tablet is required. Not only tablets may be coated, but granules, beads, gum pieces, candies and nuts may all be coated. Various pharmaceutical products, nutraceutical products and food supplements on the market today may be top coated with this clear gloss composition to enhance the appearance of the product.

As a second illustrative example, the following coating composition was produced:

Example 2

| Material | Quantity |
| --- | --- |
| MARCOAT ™ 125 | 10.0 |
| Hydrolyzed Starch Product (DE 25) | 7.5 |
| Polyethylene Glycol (MW 8000) | 0.5 |
| Water | 82 |

This is a typical clear coating solution with a ratio of shellac to hydrolyzed starch products being 1:3. This solution provides 10.5% solids and may be used in the same manner as Example 1. The hydrolyzed starch product was Maltrin M250. If a low weight gain is required on the product, this system may be diluted to 5% solids to improve uniformity of the coating. Any of the formulation examples illustrated herein may be diluted to spray at low solids or concentrate their spray at higher solids, up to 20% solids. However, at high solids, gloss may be reduced.

The following three examples, Examples 3, 4 and 5 illustrate use of other plasticizers used alone or in combination.

Example 3

| Material | Quantity |
| --- | --- |
| MARCOAT ™ 125 | 13.2 |
| Hydrolyzed Starch Product (DE 18) | 6.5 |
| Polyethylene Glycol (MW 3350) | 0.2 |
| Water | 80.1 |

Example 4

| Material | Quantity |
| --- | --- |
| MARCOAT ™ 125 | 12.0 |
| Hydrolyzed Starch Product (DE 18) | 6.0 |
| Polyethylene Glycol (MW 3350) | 1.0 |
| Water | 81.0 |

Example 5

| Material | Quantity |
| --- | --- |
| MARCOAT ™ 125 | 12.0 |
| Hydrolyzed Starch Product (DE 18) | 6.0 |
| Polyethylene Glycol (MW 8000) | 0.5 |
| Propylene Glycol | 0.5 |
| Water | 81.0 |

All of these composition formulations may be used to coat at the concentrations illustrated and produce a very glossy finish. The hydrolyzed starch product in Examples 3, 4 and 5 was Maltrin M180. Example 3 produces a solution of 10% solids and Examples 4 and 5 produce a solution of 11% solids. The formulations may be adjusted to concentrations of 5% to 15% solids and readily coated to give a very glossy finish.

The following Example 6 illustrates a coating composition which may be colored. The following Example 6 demonstrates the use of colorants such as titanium dioxide, D&C yellow 10 lake and FD&C yellow 6 lake.

Example 6

| Material | Quantity |
| --- | --- |
| MARCOAT ™ 125 | 13.6 |
| Hydrolyzed Starch Product (DE 18) | 6.7 |
| Polyethylene Glycol (MW 8000) | 1.6 |
| Titanium Dioxide | 2.1 |
| D&C yellow 10 lake | 1.1 |
| FD&C yellow 6 lake | 0.1 |
| Water | 74.8 |

Example 6 illustrates a coating solution with 15% solids. The hydrolyzed starch product was Maltrin M180. This coating composition may be sprayed at 15% solids and produce a very glossy yellow finish on tablets or other materials such as granules, beads, gum pieces, candies and nuts. No top coat is needed to give a glossy finish.

Another illustrative Example is shown in Example 7 wherein the colorants titanium dioxide, talc and FD&C blue 1 lake are used as colorants. This produces a 15% solids solution. The formulation of Example 7 uses Maltrin M180 and produces a very glossy and uniform blue finish in a standard coating operation in a Wurster column.

Example 7

| Material | Quantity |
| --- | --- |
| MARCOAT™ 125 | 13.7 |
| Hydrolyzed Starch Product (DE 18) | 6.7 |
| Polyethylene Glycol (MW 8000) | 2.0 |
| Titanium Dioxide | 1.24 |
| Talc | 1.24 |
| FD&C blue 1 lake | 0.38 |
| Water | 74.74 |

Another illustrative example which includes pearlescent pigments is illustrated in example 8. The pearlescent pigments are enhanced in the glossy coating composition of the present invention.

Example 8

| Material | Quantity |
| --- | --- |
| MARCOAT ™ 125 | 13.6 |
| Hydrolyzed Starch Product (DE 20) | 7.6 |
| Polyethylene Glycol (MW8000) | 1.6 |
| Candurin Wine Red | 2.4 |
| Water | 74.8 |

The coating composition of Example 8 produces a 15% solid solution. The Candurin Red Wine is a pigment available from EM Industries, Hawthorne, N.Y. 10592. The coating composition of Example 8 produces a very glossy pearlescent finish on tablets. This formulation produces an elegant finish on uncoated tablets at 2.5% weight gain.

Flavors and sweeteners may be added to the system to enhance the taste and mouth feel on the coating without diminishing the gloss.

The coating composition solutions as illustrated in Examples 1 through 8 are easily prepared and have good stability for several days. However, it would be desirable to prepare the solution at a much higher concentration for storage and distribution. However, at higher concentrations the solutions are stable for only about a day. In order to be able to prepare the coating composition in advance, store it and ship it to a coater, it would be very desirable and advantageous to have the solution stable for a period of time and preferably for at least three months. However, in accordance with the present invention, it has been discovered that mixing plasticizers and other resins with the shellac solution produces an incompatible system. Without stabilization in accordance with the present invention, it appears that an interaction between the ammoniated shellac, the plasticizers and the hydrolyzed starch product leads to degraded products. Either the solids form a hard deposit or the total system gels. In either case, the material is not useable for coating. The higher the concentration, the faster the degradation takes place.

In accordance with the present invention, it has been found that the coating solution may be stabilized by the addition of salts of ethylene diamine tetraacetic acid (EDTA) to the solution to prevent the degradation. The salts of EDTA may be disodium, trisodium and tetrasodium salts of EDTA and mixtures of disodium, trisodium and tetrasodium salts of EDTA. Mixtures of disodium, trisodium and tetrasodium salts of EDTA stabilize the solution at about 1% of the solution. The addition of salts of EDTA permits the preparation of solutions with 10% to 40% solids. These solutions will have a shelf life of three or more months. This will permit the preparation of high gloss coating solutions for the commercial market, including some storage, shipping time and storage and application time of the coater, as well as other applications and processes which require time after manufacture of the coating composition.

The following are illustrative examples of stabilized coating composition solutions in accordance with the present invention and are given by way of illustration and not by way of limitation.

Example 9

| Material | Quantity |
| --- | --- |
| MARCOAT ™ 125 | 36 |
| Hydrolyzed Starch Product (DE 18) | 18 |
| Polyethylene Glycol (MW8000) | 3 |
| EDTA Salts | 1 |
| Water | 42 |

The coating solution of Example 9 is a typical clear coating solution having 30% solids with a ratio of 1 part shellac to 2 parts hydrolyzed starch product. This solution may be used in the same manner as Example 1 by diluting it 2:1 with water. If a low weight gain is required, this coating composition may be diluted to 5% solids to improve uniformity of the coating. Any of the formulations may be diluted to spray at low solids or left concentrated to spray at higher solids up to 20% solids. At high solids, the gloss may be reduced.

Some other examples of stabilized coating composition solutions utilizing other plasticizers alone or in combination are as follows.

Example 10

| Material | Quantity |
| --- | --- |
| MARCOAT ™ 125 | 36 |
| Hydrolyzed Starch Product (DE 20) | 18 |
| Propylene Glycol | 2 |
| EDTA Salts | 1.2 |
| Water | 42.8 |

Example 11

| Material | Quantity |
| --- | --- |
| MARCOAT ™ 125 | 34.0 |
| Hydrolyzed Starch Product (DE 18) | 17.0 |
| Polyethylene Glycol (MW3550) | 5.0 |
| EDTA Salts | 0.8 |
| Water | 43.2 |

Example 12

| Material | Quantity |
| --- | --- |
| MARCOAT ™ 125 | 36.0 |
| Hydrolyzed Starch Product (DE 18) | 18.0 |
| Propylene Glycol | 1.5 |
| Polyethylene Glycol (MW8000) | 1.5 |
| EDTA Salts | 1.0 |
| Water | 42.0 |

The stabilized coating composition solutions of Examples 10, 11 and 12 may be diluted to coat at concentrations of 5% to 15% solids and give a very glossy finish. Example 10 illustrates a coating composition solution with 29% solids. Example 11 illustrates a coating composition with 30.5% solids. Example 12 illustrates a coating composition with 30% solids.

An example of a stabilized coating composition solution with colorants is as follows.

Example 13

| Material | Quantity |
| --- | --- |
| Material Quantity of Example 9 | 40.0 |
| Pigment Dispersion | 12.0 |
| Water | 48.0 |

Example 13 utilizes 40 parts of the solution of Example 9 which would provide 12 parts of solids since Example 9 is a 30% solids solution. The coating composition solution of Example 13 contains 16.8% solids and may be sprayed at 16.8% solids to produce a very glossy yellow finish on tablets or other materials such as granules, beads, gum pieces, candies and nuts. No top coat is needed to give a glossy finish. The pigment dispersion is 40% solids and contains titanium dioxide and FD&C yellow 5 lake. This dispersion may be a SPECTRASPRAY (SS) made by Sensient Pharmaceutical Ingredients (SPI), of South Plainfield, N.J. 07080. It is preferable that colored systems be prepared from formulations like that illustrated in Example 9, which has a plasticizer level of 10% of the combined weight of the shellac and the hydrolyzed starch product. It is preferable to use formulations with plasticizer at 10% or higher of the combined shellac and hydrolyzed starch product content when using pigments. Example 11 also provides a preferred formulation for pigmenting since it is plasticized at 19.6% of the shellac and hydrolyzed starch product content. Formulations with lower level of plasticizer are preferred for clear coating.

Another example of a colored coating composition is illustrated in Example 14.

Example 14

| Material | Quantity |
| --- | --- |
| Material Quantity of Example 11 | 40.0 |
| SS D619 | 10.0 |
| Ethyl Vanillin | 0.5 |
| Aspartame | 0.1 |
| Water | 49.4 |

The coating solution of Example 14 contains 16.6% solids and may be sprayed at 16.6% solids to produce a very glossy deep red finish. SPECTRASPRAY D619 contains FD&C red 40 lake and dye with titanium dioxide. Flavors and sweeteners may be added to this system to enhance the taste and mouth feel of the coating without diminishing the gloss. Organoleptic agents may be added separately or they may be added to the coating composition represented by Example 11 or to the SPECTRASPRAY represented by SS D619.

The solutions of Examples 9 through 14 were observed to remain stable for more than three months after manufacture of the coating composition solution.

In view of the above, the present invention may be embodied in other specific forms without departing from the spirit or essential attributes thereof and, accordingly, reference should be made to the appended claims, rather than to the foregoing specification as indicating the scope of the invention.

What is claimed is:

1. An edible film coating composition, comprising:
shellac in an aqueous-based ammonia solution;
a hydrolyzed starch product having a dextrose equivalent of 10 or greater, wherein the ratio of said shellac to said hydrolyzed starch product is from about 1/1 to 1/4; and
an effective amount of a plasticizer for making the composition non-sticky when applied as a coating; and wherein a high gloss coating may be achieved.

2. An edible film coating composition in accordance with claim 1 wherein the ratio of shellac to hydrolyzed starch product is from about 1/2 to about 1/3.

3. An edible film coating composition in accordance with claim 1 wherein said hydrolyzed starch product has a dextrose equivalent in the range of 15 to 30.

4. An edible film coating composition in accordance with claim 3 wherein said hydrolyzed starch product has a dextrose equivalent in the range of 18 to 25.

5. An edible film coating composition in accordance with claim 1 wherein said shellac is provided in a concentration of about 25% aqueous solution.

6. An edible film coating composition in accordance with claim 1 wherein said shellac is provided in a concentration of about 20% aqueous solution.

7. An edible film coating composition in accordance with claim 1 wherein said plasticizer is selected from the group consisting of triacetin, triethylcitrate, polyethylene glycol (molecular weight 200-8000), propylene glycol, glycerine, glycerol monostearate, diacetylated monoglyceride and polysorbate.

8. An edible film coating composition in accordance with claim 7 wherein the plasticizer is polyethylene glycol having a molecular weight in the range of 400 to 8000.

9. An edible film coating composition in accordance with claim 8 wherein the plasticizer is polyethylene glycol having a molecular weight of 1000 or higher.

10. An edible film coating composition in accordance with claim 1 wherein the amount of plasticizer is 1% to 25% of the combined weight of said shellac and said hydrolyzed starch product.

11. An edible film coating composition in accordance with claim 10 wherein the amount of plasticizer is 1% to 10% of the combined weight of said shellac and said hydrolyzed starch product.

12. An edible film coating composition in accordance with claim 11 wherein the amount of plasticizer is 2% to 5% of the combined weight of the shellac and the hydrolyzed starch product.

13. An edible film coating composition in accordance with claim 1 wherein the plasticizer is polyethylene glycol with a molecular weight of about 3350.

14. An edible film coating composition in accordance with claim 1 wherein the plasticizer is polyethylene glycol with a molecular weight of about 8000.

15. An edible film coating composition in accordance with claim 1 including a colorant in an amount of 20% to 40% of the combined weight of the shellac and the hydrolyzed starch product.

16. An edible film coating composition in accordance with claim 15 wherein the colorant is FD&C lakes and dyes.

17. An edible film coating composition in accordance with claim 15 wherein the colorant is D&C lakes and dyes.

18. An edible film coating composition in accordance with claim 15 wherein the colorant comprises titanium dioxide.

19. An edible film coating composition in accordance with claim 15 wherein the colorant comprises iron oxides.

20. An edible film coating composition in accordance with claim 15 wherein the colorant comprises pigments that are deposited on mica to produce a pearlescent effect.

21. An edible film coating composition in accordance with claim 15 wherein the amount of plasticizer is 5% to 20% of the combined weight of the shellac and hydrolyzed starch product.

22. An edible film coating composition in accordance with claim 15 wherein the composition is comprised of an aqueous solution with 5% to 20% solids.

23. An edible film coating composition in accordance with claim 22 comprised of an aqueous solution containing 10% to 25% solids.

24. A stable coating solution for use in forming an edible film coating, comprising:
shellac in an aqueous-based ammonia solution;
a hydrolyzed starch product having a dextrose equivalent of 10 or greater, wherein the ratio of said shellac to said hydrolyzed starch product is from about 1/1 to 1/4;
an effective amount of a plasticizer for making the composition non-sticky when applied as a coating; and
an effective amount of ethylene diamine tetraacetic acid salt to make the solution remain stable for at least three months.

25. A stable coating solution in accordance with claim 24 wherein the solution comprises up to 40% solids.

26. A stable coating solution in accordance with claim 24 wherein the salts of ethylene diamine tetraacetic acid comprise disodium, trisodium and tetrasodium salts of ethylene diamine tetraacetic acid.

27. A stable coating solution in accordance with claim 26 wherein the concentration of ethylene diamine tetraacetic acid salt is about 0.5% to 2% of the solution.

28. A stable coating solution in accordance with claim 24 comprised of approximately 9 parts shellac, approximately 18 parts of a hydrolyzed starch product having a dextrose equivalent of approximately 18, approximately 3 parts of polyethylene glycol (molecular weight of approximately 8000) and 1 part being salt of ethylene diamine tetraacetic acid with the remainder being water.

29. A stable coating solution in accordance with claim 24 comprised of approximately 9 parts shellac, approximately 18 parts of a hydrolyzed starch product having a dextrose equivalent of approximately 20, approximately 2 parts of propylene glycol, approximately 1.2 parts ethylene diamine tetraacetic acid salt with the remainder being water.

30. A stable coating solution in accordance with claim 24 comprising approximately 8.5 parts shellac, approximately 17 parts of a hydrolyzed starch product having a dextrose equivalent of 18, approximately 5 parts of polyethylene glycol and approximately 0.8 parts of ethylene diamine tetraacetic acid salt and the remainder being water.

31. A stable coating solution in accordance with claim 24 comprising approximately 9 parts shellac, approximately 18 parts of a hydrolyzed starch product with a dextrose equivalent of approximately 18, approximately 1.5 parts propylene glycol, approximately 1.5 parts polyethylene glycol (molecular weight of about 8000) and approximately 1 part ethylene diamine tetraacetic acid salt with the remainder being water.

32. A stable coating solution in accordance with claim 28 which comprises a pigment dispersion to provide coloring.

33. A stable coating solution in accordance with claim 30 comprising a colorant dispersion which includes FD&C red 40 lake and dye and titanium dioxide.

* * * * *